US005256141A

United States Patent [19]

Gencheff et al.

[11] Patent Number: 5,256,141

[45] Date of Patent: Oct. 26, 1993

[54] BIOLOGICAL MATERIAL DEPLOYMENT METHOD AND APPARATUS

[76] Inventors: Nelson Gencheff, 117 Lakeshore Rd., Grafton, Wis. 53024; Carl W. Christensen, 7463 N. Beach Ct., Fox Point, Wis. 53217

[21] Appl. No.: 995,105

[22] Filed: Dec. 22, 1992

[51] Int. Cl.$^5$ .................... A61M 31/00; A61M 29/00

[52] U.S. Cl. .................... 604/53; 604/101; 604/265

[58] Field of Search .................... 606/104; 604/96, 100, 604/101, 113, 114, 265

[56] References Cited

U.S. PATENT DOCUMENTS

| | | | |
|---|---|---|---|
| 4,423,725 | 1/1984 | Baran et al. | 604/43 |
| 4,610,662 | 9/1986 | Weikl et al. | 604/53 |
| 4,636,195 | 1/1987 | Wolinsky | 604/53 |
| 4,785,823 | 11/1988 | Eggers et al. | 128/692 |
| 4,944,745 | 7/1990 | Sogard et al. | 604/194 |
| 5,129,883 | 7/1992 | Black | 604/101 |

FOREIGN PATENT DOCUMENTS

| | | | |
|---|---|---|---|
| 3806458 | 9/1959 | Fed. Rep. of Germany . | |
| 2513868 | 10/1975 | Fed. Rep. of Germany . | |
| 85/02779 | 2/1985 | PCT Int'l Appl. . | |
| 9116945 | 11/1991 | PCT Int'l Appl. | 604/96 |
| 721110 | 3/1980 | U.S.S.R. . | |
| 1069826 | 1/1984 | U.S.S.R. . | |
| 1228821 | 5/1986 | U.S.S.R. . | |
| 2219510 | 12/1989 | United Kingdom . | |

OTHER PUBLICATIONS

Haudenschild, C. C., "Growth control of endothelial cells in atherogenesis and tumor angiogenesis", Advances in Microcirculation, 9 (1980) 226-251.

Ross, R., "The pathogenesis of atherosclerosis", in Braunwald, E. (ed): Heart Disease, 3d Edition, Saunders WB, 1988, 1135-1152.

Ross, R. and J. Glomset, "Atherosclerosis and arterial smooth muscle cell", Science, 180 (1973) 1332.

Schneider et al, "Confluent durable endothelialization of endarterectomized baboon aorta by early attachment of cultured endothelial cells", *J. Vasc Surg*, 11:365-372, 1990.

Flugelman et al, "Genetically engineered endothelial cells remain adherent and viable after stent deployment and exposure to flow in vitro", *Circ Res* 70:348-354, 1992.

Jarrell et al, "Use of freshly isolated capillary endothelial cells for the immediate establishment of a monolayer on a vascular graft at surgery", *Surgery* 100(2):392-399, 1986.

*Primary Examiner*—Jerome L. Kruter

*Attorney, Agent, or Firm*—Haugen and Nikolai

[57] ABSTRACT

The invention involves a system for the deployment of biologically active materials in a bodily passage, particularly in vascular wall tissue, in the form of an elongated multi-lumen catheter having a plurality of serially situated functional zones. One embodiment includes an externally accessed dispersion zone adapted to address a vascular segment and having a dispersion chamber subtending a major arc of the vascular circumference provided with a pattern of openings for deploying biologically active materials in the vascular segment and supplied through an externally connected lumen. An electrode member is provided associated with the dispersion zone for applying a controlled electrical charge to the biologically active material at the point of deployment. A pair of spaced inflatable balloons define proximal and distal occlusion zones for temporarily occluding normal vascular blood flow in the vascular segment during deployment of the biologically active materials. A flow bypass lumen connects proximal and distal infusion port zones flanking the occlusion zones and maintaining blood flow about and beyond the vascular segment during occlusion. A control system is provided for controlling operation of the deployment system including electrical input capable of the time-variable modulation of the charge applied by the electrode means.

26 Claims, 1 Drawing Sheet

10
12
14
16
18
20
22
24
26
28
30
32
34
40
42
44
46
48
50
54
56
126
128
130
132
134
228
234
3
5

BIOLOGICAL MATERIAL DEPLOYMENT METHOD AND APPARATUS

BACKGROUND OF THE INVENTION

I. Field of the Invention

The invention is directed generally to a catheter or other invasive vascular navigating device intended to enable deployment of biologically active materials. More particularly, the invention involves a vascular catheter system for the electrical charge mediated deployment of biologically active materials into specific segments of living blood vessels. This includes transplanting biologically functional autologous vascular endothelium into blood vessels whose endothelium and subendothelial structures have been damaged as well as altering subendothelial biology by the electrical application of metabolic activators or inhibitors.

II. Description of the Related Art

Coronary artery disease is a significant problem throughout the world, and it is among the major consequences of injured endothelial cells. If left to its natural history, coronary artery disease invariably leads to death. The past two decades of cardiovascular research have resulted in the birth and growth of interventional cardiovascular procedures which have made a major impact on the morbidity and mortality of patients with this disease. According to 1992 statistics, an estimated 750,000 patients with coronary artery disease will undergo coronary artery balloon angioplasty or atherectomy to open a blocked artery. However, since the first percutaneous transluminal coronary angioplasty (PTCA) performed in 1977 by Andreas Gruentzig, cardiovascular interventionalists have been witness to generally disappointing long-term results with respect to the post-PTCA vessel patency. Approximately 30% to 50% of the treated patients will have recurrence (restenosis) of their arterial obstructions and will require further angioplasty treatment or open heart surgery.

Restenosis of angioplasted vascular segments has prompted a multifaceted, international research campaign attempt to improve post-PTCA long-term vessel patency. Much of this research has been focused on improving balloon catheter designs, understanding lesion characteristics, improving patient selection for angioplasty procedures and elucidating the pathophysiology of restenosis.

A major cause of this restenosis is the absence or disruption of the normal cells (endothelial cells) that line the internal surface of a normal arterial segment. This cell lining, known as vascular endothelium, is often disrupted or destroyed by the atherosclerotic disease process and by the previously mentioned stenosis reduction or removal procedures. Maintaining vascular endothelial integrity is important as it performs a variety of vital functions necessary to support life. These functions are contingent upon the presence of morphologically intact and biologically functional endothelial cells and their intimate association with subendothelial structure. Disruption of the framework of this biological system causes the endothelial cells to become dysfunctional, and it is this critical event which sets the stage for the onset or recurrence of vascular disease and its devastating progression.

In this regard, vascular smooth muscle cell proliferation appears to be a pivotal event in the pathology of restenosis. Smooth muscle cell proliferation is, in part, triggered by the mitogenic properties of platelet-derived growth factor (PDGF). However, it is generally believed that more than one mitogenic activator is responsible for this process. There is further evidence suggesting that endothelial cells help to modulate vascular smooth muscle cell biology and that when endothelial cells become dysfunctional, vascular smooth muscle cells favor a synthetic (proliferative) state. Further discussion is provided by, for example, Haudenschild, C. C., "Growth control of endothelial cells in atherogenesis and tumor angiogenesis", Advances in Microcirculation, 9 (1980) 226-251; Ross, R., "The pathogenesis of atherosclerosis", in Braunwald, E. (ed): Heart Disease, 3d Edition, Saunders W. B., 1988, 1135-1152; Ross, R. and J. Glomset, "Atherosclerosis and arterial smooth muscle cell", Science, 180 (1973) 1332.

Since PTCA traumatizes vascular endothelium and subendothelial structures, it triggers a cascade of biological events which may lead to smooth muscle cell proliferation. To a great extent, this PDGF-mediated process may be held in check by platelet inhibitors and heparin sulfate. However, because PDGF, and other smooth muscle mitogens, are not only released by platelets, but also by dysfunctional endothelial cells, uncontrolled smooth muscle cell proliferation can still occur.

Vascular endothelial cells grow in an obligate monolayer attached by tight junctions and gap junctions. Maintenance of this structural design is essential for the normal biological function of endothelial cells and this framework is, in part, accomplished through a type IV collagen matrix upon which endothelial cells reside. If endothelial cells are unable to adhere to a given surface, they become nonviable. In vivo placement of endothelial cells upon this collagen matrix is inherently problematic because laminar flow produces forces of shear stress resulting in an intravascular environment which is non-conducive for endothelial cell attachment. However, freshly endarterectomized aortas incubated in vitro, in a low flow, low pressure environment with homologous aortic endothelial cells for 20 minutes result in rapid endothelial cell attachment, as reported by Schneider et al, "Confluent durable endothelialization of endarterectomized baboon aorta by early attachment of cultured endothelial cells, *J. Vasc Surg* 11:365-372, 1990. In vivo exposure of these attached cells to laminar blood flow and pressure for one hour yields a thromboresistant, confluent and durable monolayer. It has also been shown that in vitro seeding of genetically engineered endothelial cells onto catheter mounted stainless steel vascular stents remain not only adherent but also viable after stent expansion and exposure to in vitro pulsatile flow (Flugelman et al, "Genetically engineered endothelial cells remain adherent and viable after stent deployment and exposure to flow in vitro", *Circ Res.* 70:348-354, 1991). Finally, endothelial cells freshly obtained from human fat and acutely seeded in vitro onto plasma coated dacron grafts for one hour, remain adherent and form confluent monolayers when exposed to flow for two hours at a shear stress of 0 to 80 dynes/$cm^2$ (Jarrell et al, "Use of freshly isolated capillary endothelial cells for the immediate establishment of a monolayer on a vascular graft at surgery, *Surgery* 100(2):392-399, 1986).

Since endothelial cells contain much of the biological armamentarium necessary to orchestrate the molecular events required to maintain a thromboresistant and homeostatic vascular milieu, it follows that if a device were available to quickly reestablish a normal endothelial monolayer immediately following angioplasty or atherectomy, the incidence of restenosis could be significantly reduced and possibly eliminated. The high flow velocities of the intravascular hemodynamic forces, however, technically limits in vivo application of endothelial seeding onto denuded intravascular surfaces.

Invasive implant devices including catheters have been proposed which deliver an electric charge to remote areas of a patient's body. One such catheter device intended for relative long-term use has been devised that applies a unidirectional negative charge to discourage microbial growth at the implant interface surface. This is shown in UK patent application GB 2 219 510. A PCT application WO 85/02779 discloses a catheter for treating tumors which delivers a high frequency heat producing current to the tumor tissue.

Other catheter devices are known that employ a plurality of spaced fluid inflated balloon devices for isolating and treating segments of blood vessels and other body passages such as trachea and urethra. Examples of such devices which also allow bypass flow around an isolated segment are found in Weikl et al (U.S. Pat. No. 4 610 662) and Baran et al (U.S. Pat. No. 4 423 725). A further multiple balloon device is illustrated in Wolinsky (U.S. Pat. No. 4 636 195).

The present invention addresses this problem by providing a new device which includes a system for deployment of biologically active materials (endothelial cells) into specific segments of living blood vessels to be reseeded with new, autologously derived endothelial cells. The invention also provides for iontophoretic delivery of pharmacologic agents into these specific vascular segments. One design aspect of the device provides for significantly diminished blood flow in the specific vascular segments of interest for a time long enough, for example, to allow cultured endothelial cells to adhere to the vascular surface. An integral bypass system permits simultaneous blood flow beyond the isolated area.

OBJECTS OF THE INVENTION

Accordingly, it is a primary object of the present invention to provide a new catheter system which will enable the electrical charge mediated deployment of biologically active materials into specific segments of living blood vessels.

A further object of the invention is to provide a catheter system capable of the electrical application of metabolic activators and/or inhibitors for altering subendothelial biology.

Another object of the invention is to provide a catheter system for transplanting biologically functional autologous endothelial cells onto blood vessels whose endothelium and subendothelial structures have been mechanically or physically perturbed.

A still further object of the invention is to provide a catheter system capable of mechanically isolating a vascular segment of interest, and deploying biologically active materials and maintaining blood flow distal to the vascular segment of interest.

Yet another object of the invention is to provide a method of deploying biologically active materials including iontophoretic delivery of pharmacologic agents into vascular segments through an externally accessed dispersion chamber.

SUMMARY OF THE INVENTION

The present invention solves many of the problems associated with the deployment of biologically active materials in vascular segments in which the deployment requires a period of flow interruption, i.e., a time to establish the biologically active material in situ for the deployment to succeed. The biological deployment system of the invention may take many forms. One important form is concerned with charge mediated deployment of endothelial cells into vascular segments having damaged vascular endothelium. The invention also provides a method of preventing or reducing repeated vascular blockages in segments where stenoses have previously been invasively treated.

One successful embodiment is in the form of an endothelial deployment catheter device. The catheter is a multi-zone, multi-lumen device that interfaces a plurality of input/output peripherals proximally and provides working zones distally. In the working portion of the catheter, a pair of spaced fluid inflatable 15 balloons having centers marked by radiopaque bands flank a controlled charge-mediated dispersion zone which includes an electrode to which a charge can be applied and a dispersion chamber or infusion lumen in contact with the electrode and having a plurality of openings through which with material of interest including an endothelial cell culture can be discharged into the vascular segment between the spaced balloons.

A further pair of zones flanking the pair of flow control balloons contain radially disposed openings which lead to a common guidewire/perfusion lumen which provides a continuous bypass conduit for blood to bypass the segment defined by the flow control balloons when one or both are inflated to reduce or curtail flow in the vascular segment of interest. A long vascular navigating zone is provided between the peripheral interface zone and the proximal isolation balloon to connect the system outside the patient. The distal portion of this zone includes the proximal bypass perfusion inflow ports.

The catheter is preferably constructed as an over-the-wire system and may conveniently be produced of quadraxially extruded polyethylene tube or similar material providing four internal lumens to accomplish the catheter functions. The lumens connect the various working zones with the peripheral interface zone. Thus, lumens independently connect the proximal and distal isolation or flow control balloons with pressure regulated fluid sources. A lumen is provided to connect the dispersion chamber with a source of the biologically active material to be delivered to the vascular segment and the guidewire/perfusion lumen carries the guidewire and includes the inlet and outlet ports for the bypass flow.

Deployment of the biologically active material through the externally accessed dispersion chamber is accomplished in conjunction with the operation of a pulsed or constant electric field provided by the externally connected electrode which is typically a perforated foil or mesh of a noble metal, such as platinum, overlaying the dispersion chamber and externally connected by a platinum wire. If operated in a pulsed mode, the pulse may be delivered by an electrical stimulator triggered by the patient's own ECG complex. The dispersion chamber of one model was 22 mm long and delivered materials through a pattern of perforations through an arc-shaped chamber that included about 240 degrees of the circumference of the catheter. The openings in the dispersion chamber cooperate with those in the electrode to produce a uniform delivery of the material contained in the dispersion chamber.

The method includes inserting the guidewire by means of a guide catheter and guidewire port and advancing the guidewire through the vascular system beyond the vascular segment to be treated. The deployment catheter device of the invention is delivered over the guidewire via the guidewire lumen. Using the radiopaque markers associated with the deployment catheter tip and isolation balloons, the dispersion chamber is positioned in the location to be treated, the balloons are inflated and a bypass flow establishes itself around the isolated segment. The electrode is energized and the biologically active material, normally a culture of endothelial cells and/or metabolic activators or metabolic inhibitors to alter the subendothelial biology are delivered through the dispersion chamber under the influence of the electric field controlled by the operator. After the cells have had time to attach, the steps may be reversed and the system removed from the patient.

Balloon pressure is monitored using manometers or other well-known devices to prevent overpressurization as the purpose of the balloons is only to occlude flow, not expand vascular size. In addition, the dispersion chamber is typically provided with a one-way pressure relief valve which remains closed unless the relative pressure within the occluded vascular segment exceeds a predetermined pressure such as 100 mm Hg. The relief valve is typically 400 $\mu$m in diameter.

The deployment device of the invention facilitates and expedites reseeding of new, biologically functional, autologous endothelium and modulates subendothelial biology by the electrical application of growth activators and/or inhibitors in specific vascular segments previously perturbed. In addition, the device of the invention is decidedly useful for many iontophoretic delivery applications. The system can be used to apply a pulsed or constant direct current stimulus to transport pharmacologic agents including cardioactive drugs such as vasodilators and other materials, for example, to specific subendothelial vascular tissue sites of interest in conjunction with the placement of the deployment device. Thus, any drug or other material susceptible to iontophoretic transport implantation may also be delivered by the system. In this manner, positively or negatively charged ions of interest are driven into the tissue of interest utilizing an applied current differential in a well-known manner. The device of the invention, in this manner, provides what amounts to be a portable system which can be used to apply iontophoretic transport techniques to any selected vascular segment of interest.

BRIEF DESCRIPTION OF THE DRAWINGS

In the drawings, wherein like numerals designate like parts throughout the several views.

DETAILED DESCRIPTION

Figures 1, 2, 3, 4, 5, 6:
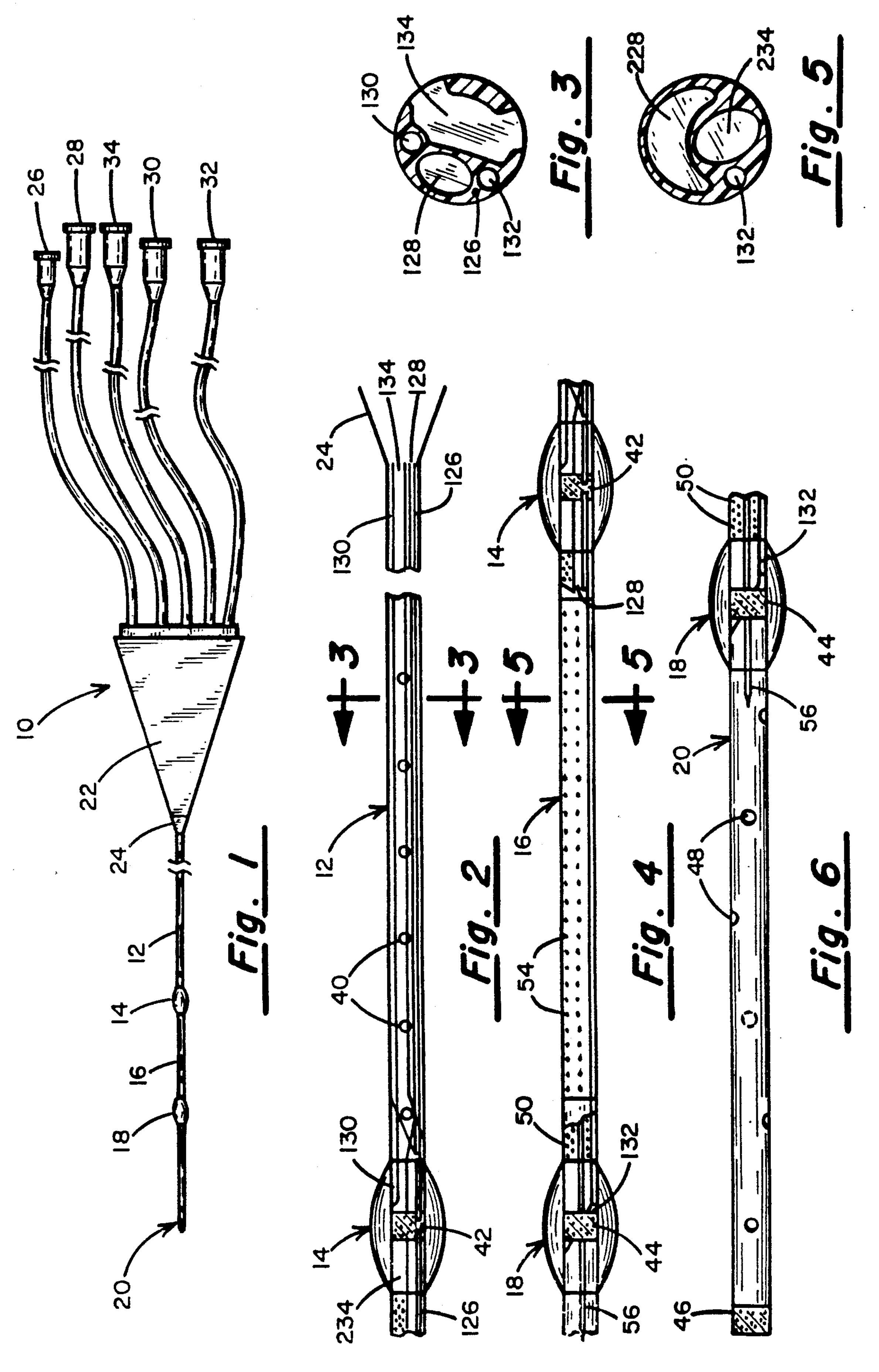
FIG. 1 is an overall schematic view of the endothelial deployment catheter device of the invention broken away where inordinate lengths are involved.
FIG. 2 is an enlarged fragmentary side view of a proximal zone of the catheter portion of the device of FIG. 1.
FIG. 3 is a sectional view taken along 3—3 of FIG. 2.
FIG. 4 is an enlarged fragmentary side view similar to that of FIG. 2 of the central zones of the catheter portion of the device of FIG. 1.
FIG. 5 is a sectional view taken along 5—5 of FIG. 4.
FIG. 6 is a view similar to those of FIGS. 2 and 4 depicting the distal zone of the catheter portion of the device.

FIG. 1 depicts an overall schematic view of the endothelial deployment device of the invention denoted generally at 10. The device includes an elongated catheter which itself is divided into a plurality of body invasive zones 12, 14, 16, 18 and 20 intended to navigate vascular passages and which connect to what may be described as a peripherals interface zone 22 located proximal of the body invasive zones and the body/catheter entry hub 24. The peripherals interface zone connects a plurality of externally accessible devices with the corresponding catheter lumens. These may include an electrical input/output single or multiple conductor plug or jack device 26, a drug or implant cell infusion port access 28, a proximal balloon inflation fluid passage port 30, a distal balloon infusion fluid port 32 and a guidewire/perfusion access port shown at 34. These are connected by appropriate means to the corresponding lumens of the catheter through the interface zone.

These and other types of access ports are common to such devices and the precise construction may vary according to the practices of those skilled in the art. For example, the guidewire or catheter is preferably constructed to be deployed using established over-the-wire vascular navigation techniques. Thus, the proximal guidewire port shown at 34 may be located, for example, close to the distal end of the proximal invasive catheter zone or segment 12. The distal port is normally an opening at the distal tip of the system so that the catheter device of the invention can be advanced over a guidewire that has been previously inserted and navigated through the vascular system of the subject to the vicinity of the area or segment of interest to be treated.

The catheter system itself, as seen in FIG. 1, is generally divided into six zones or longitudinal segments, the most proximal of which is the peripheral interface zone 22 which further contains intrusion sealing hub 24. The remaining zones are pictured in FIGS. 2–6 and represent multi-lumened segments of an elongated tubular catheter. The electrical port 26 connects to an insulated platinum wire 126 embedded within the substance of the polyethylene material (FIGS. 2–4) and used in association with an electrode described below. The remaining ports are extensions of four other lumens within the endothelial deployment device as will be discussed below. The catheter itself may preferably be constructed of quadraxially extruded polyethylene tube providing the desired number, size and configuration of internal lumens. Of course, it is contemplated that other materials and techniques of manufacture may more appropriately be employed if indicated.

Zones 14 and 18 consist of the proximal and distal balloons, respectively. The separation between the balloons defines the vascular span occluded when the balloons are inflated and includes the diffusion chamber. Inflation of these balloons is accomplished using a radiopaque contrast solution which is infused to the balloon 14 through the proximal balloon inflation lumen 130 and distal balloon zone 18 is inflated via the distal balloon inflation lumen 132. Radiopaque marker bands are used to define the center of each balloon as at 42 and 44. This aids in navigation of the catheter to precise placement in the vascular system. The balloons typically measure 6 mm in length and inflated balloons conform generally to an ellipsoid shape. The maximum diameter occurs at the center of the balloon which, when fully inflated, may measure approximately 2–5 mm. They are manufactured according to known technology from a highly compliant polyethylene blended polymer, polyethylene terephthalate (PET), nylon, or other material in a well-known manner.

The design of the particular balloons used with the endothelial deployment device of the present invention affords minimal compression of the vascular surfaces upon inflation of the balloons while accomplishing physical interruption of blood flow between the balloons. Thus, it is not the purpose of the balloons in the present invention to compress stenoses as is generally the case with typical angioplasty devices, but merely to interrupt blood flow so that the desired drug/cell infusion operation can take place without exposure to flowing fluid. Manometers or other well-known pressure monitoring devices (not shown) are connected to monitor the balloon inflation pressure.

Segments or zones 12 and 14 are shown in greater detail in the enlarged fragmentary view of FIG. 2. Zone 12 typically measures approximately 840 mm in length and extends from the distal aspect of hub 24 to the origin of the proximal balloon zone 14. Approximately 25 mm of the distal end provides the input access for the vascular flow to bypass zones 14, 16 and 18. This portion of zone 12 contains a plurality of perfusion inflow ports which are directly connected to the guidewire/-perfusion lumen 134 (FIG. 3). One successful embodiment uses two series of six serially spaced perfusion inflow ports 40, one series of which is illustrated in FIG. 2. Typically, the perfusion inflow ports are approximately 0.5 mm in diameter and spaced about 4.0 mm apart.

The most distal zone of the device 20 in one embodiment extends 26 mm in length from the terminal portion of the distal balloon zone 18 to the distal tip marked by a radiopaque band 46 of the endothelial deployment device. The outer diameter of distal zone 20 tapers from approximately 1.5 mm at its origin to about 1.2 mm at the distal terminal end. The zone 20 is provided with a plurality of spirally arranged outflow perfusion ports 48 to return the bypassed fluid to the vascular passage of interest each measuring approximately 0.5 mm in diameter, it being further understood that the terminal end or distal may also be open to reduce flow restriction and accommodate the guidewire. Each of the outflow ports 48 is connected directly to lumen 234 which is an extension of lumen 134 but of slightly different crossectional character and the outflow ports are separated from each other by approximately 4 mm. A radiopaque tip marker band 46 similar to those associated with the midpoints of the proximal and distal balloon zones 14 and 18 at 42 and 44 is provided.

It will readily be appreciated that blood flowing directly into lumen 134 in the distal portion of zone 12, then, bypasses 14, 16 and 18 and exits through the openings 48 and the tip in zone 20. In this manner, the blood flow entirely bypasses the segment of the vessel of interest separated and occluded by balloons 14 and 18, i.e., zone 16. Of course, should the catheter be used to address a vessel in which the flow is in the opposite direction, the bypass system will accommodate reverse flow.

An important aspect of the invention is the dispersion system associated with zone 16. Zone 16 includes the dispersion chamber by means of which the drug/cell infusion and implantation takes place in accordance with the invention. Zone 16 is typically approximately 22 mm in length but may vary according to clinical needs. The dispersion chamber is supplied via port 28 which continues through zone 12 in the form of lumen 128 (FIG. 3) and, in zone 16, the lumen at 228 (FIG. 5) takes the form of a kidney-shaped crossection having an outer arc consuming up to approximately 240° of the circumference of the catheter as shown at 228 in FIG. 5. The dispersion chamber of zone 16 is designed as a closed well system, isolated from the other distinct spaced parallel lumens within the catheter system. The dispersion system of lumen 228 is used to deploy the endothelial cell culture and growth activators and inhibitors as well as medicinal materials as desired. The dispersion chamber communicates with the isolated vascular segment between balloon zones 14 and 18 through a plurality of perforations 50 in the wall of the catheter defining the lumen 228 which typically are arranged in a rectangular pattern and measure approximately 250 microns (μm) in diameter and are spaced about 500 μm apart. The exterior portion of the chamber is coated with a similarly perforated thin platinum foil member or platinum mesh screen 52 having perforations or openings 54 which are open to the exterior of the catheter. The platinum further serves as an electrode to produce an electric current or field using power originating from an external source connected to the input 26 and from there to the platinum foil or mesh via isolated conductor 126. The single platinum wire 126 typically measures approximately 100 μm in diameter and is preferably isolated by being embedded in the substance of the polyethylene or other catheter construction material and thereby also being electrically insulated from the other structures in the endothelial deployment device.

Materials to be deployed from the dispersion chamber are infused through the drug/cell infusion port 28, conducted through the several connected continuing lumen shapes as at 128 to the dispersion chamber lumen 228 in zone 16 where they are distributed via the openings 50 and 54 to the vascular site of interest. The use of the electrical field or current may be used in the deployment of the biologically active materials, specifically, the vascular endothelial cells.

The distal aspect of the dispersion chamber segment or zone 16 contains a one-way pressure relief valve 56 (FIG. 4) which is approximately 400 μm in diameter and which remains closed unless relative pressure within the occluded vascular segment exceeds a predetermined maximum, typically 100 mm Hg. The valve, of course, prevents vascular damage due to inadvertent overpressurization of the vessel of interest during infusion into segment 16.

The typical overall length of the endothelial device of the invention is approximately 1,115 mm and may be delivered over a guidewire into a blood vessel of interest using any one of several guiding catheter devices. The marker bands, of course, are used in conjunction with fluoroscopic observation to permit accurate vascular navigation of the distal tip of the device as well as the centers of the proximal and distal balloons for more precise positioning in the vascular system of the location of the segment to be treated.

The procedure for operation of the system of the invention begins with the insertion of a guide catheter into the arterial system of the subject, typically through the femoral artery. A guidewire is advanced through the vascular system via the guide catheter until the guidewire tip reaches a point at or just beyond the vascular segment of interest. This is typically beyond the location of a stenosis or lesion which has just been subjected to a balloon angioplasty or atherectomy procedure. At this point, a portion of the guidewire, of course, still extends through the guide catheter to a point outside the body. The endothelial deployment device of the invention can then be advanced over the wire so that the wire is passed through the hollow lumen beginning at the distal end and through the lumen sequence 234, 134 and protruding out of guidewire port 34 or other proximal guidewire port opening.

The multi-lumenal catheter system of the endothelial deployment device of the invention is then advanced over the wire through the vascular system to the site of the vascular segment of interest. In accordance with the invention, the radiopaque markers 42 and 44 can be used to properly align the balloons 14 and 18 flanking the vascular segment of interest. Once the system is in place, the balloons 14 and 18 can be inflated by introducing fluid into the proximal and distal balloon ports which are connected to a fluid source in a well-known manner.

Once the balloons are properly inflated, a bypass blood flow is established, the blood flow in the vascular segment between the proximal and distal balloons of the endothelial deployment device having been physically interrupted so that the walls of the vascular segment to be treated are temporarily removed from the path of flowing fluid. This condition is a prerequisite to endothelial cell implantation.

The perforated platinum foil electrode disposed between the dispersion chamber and the segment of vessel of interest can now be energized in any desired manner. For example, the wire 126 may be used to deliver current in a constant or pulsed fashion which may be triggered by the patient's own ECG complex via an electrical stimulator. Duration of the current may be adjusted such that a pulse of current is initiated on a peak of the patient's R- wave and terminated prior to the vulnerable period of repolarization (e.g., the ascending slope of the T wave). This is done in conjunction of just following deployment of biologically active materials introduced via port 28 and lumens 128 and 228 and ultimately through the openings 50 and 54 in the dispersion chamber segment 16 and platinum foil. In accordance with a main application of the invention, the biologically active materials typically contain an endothelial cell culture together with other materials to promote and establish attachment and growth.

Inasmuch as cultured endothelial cells may preferably migrate toward a variably charged electrode, by variably charging the platinum foil, the vascular segment of interest may have a slight charge. It is, of course, understood that an exterior electrical common exists in order to complete such an electrical circuit. This may aid in the delivery of endothelial cells to the wall of the vascular segment of interest. Replication of the electrical charge together with the maintenance of the occluded or flow-free state of the vascular segment may promote the tendency of the endothelial cells to adhere to the surface of the interior of the vessel of interest. In this manner, the endothelial cells may be able to attach and resume normal biological activity such that they will not be dislodged and swept away by normal blood flow. At this point, the proximal and distal balloons can be deflated and the deployment device removed by reversing the insertion steps.

By using the device of the invention, the endothelial cells or other biologically active material can be readily dispersed to the vascular segment of interest, in vivo, using the flow bypass system. Cell adherence may be sped up by applying the electric charge during the deployment step. Subsequent normal growth should reestablish normal vascular endothelium and prevent or retard restenosis in the vascular segment involved.

This segment has been described in this application in considerable detail in order to comply with the Patent Statutes and to provide those skilled in the art with the information needed to apply the novel principles and to construct and use such specialized components as are required. However, it is to be further understood that the invention can be carried out by specifically different equipment and devices and that various modifications can be accomplished without departing from the scope of the invention itself.

We claim:

1. A system for the deployment of biologically active material in vascular wall tissue of a vascular segment of interest, the device being in the form of an elongated multi-lumen catheter having a plurality of serially situated functional zones comprising:

an externally accessed dispersion zone adapted to address a vascular segment and having a perforated dispersion lumen chamber subtending a major arc of the vascular circumference provided with a pattern of openings for deploying biologically active materials in the vascular segment supplied through an externally connected lumen;

an electrode means with the dispersion zone for applying a controlled electrical charge to the biologically active material at the point of deployment;

a pair of spaced inflatable balloons defining a pair of occlusion zones for temporarily occluding normal vascular blood flow in the vascular segment of interest during deployment of the biologically active materials;

flow bypass means comprising a lumen connecting proximal and distal infusion port zones for maintaining at least a minimum blood flow about and beyond the vascular segment of interest during the occlusion thereof; and control interface means for controlling operation of the system including means capable of the time-variable modulation of the charge applied by the electrode means.

2. A vascular catheter adapted as a biologically active species deployment device comprising:

a main catheter device having two spaced balloon elements expansible against adjacent walls to occlude flow in a vascular segment and define a deployment zone therebetween;

a deployment zone further including;

a deployment chamber for delivering biologically active materials to the vascular wall during the period of flow occlusion;

an electrode means for delivering a charge to the biologically active material during the delivery thereof; and flow bypass means providing an alternate path for vascular flow around the occluded vascular segment.

3. The system of claim 1 wherein the biologically active materials include endothelial cells.

4. The system of claim 2 wherein the biologically active materials include endothelial cells.

5. The system of claim 1 wherein the biologically active materials include material selected from the group consisting of metabolic activators and inhibitors and iontophoretic transportable pharmacologic agents.

6. The system of claim 2 wherein the biologically active materials include material selected from the group consisting of metabolic activators and inhibitors and iontophoretic transportable pharmacologic agents.

7. The system of claim 2 wherein the deployment chamber zone is part of an infusion lumen and subtends a major arc of the vascular circumference and the biologically active material is dispersed through a pattern of perforations.

8. The system of claim 7 wherein the electrode means further comprises control means capable of time-variable modulation of the applied charge.

9. The system of claim 7 wherein the electrode means forms a layer parallel to the deployment layer and contains openings permitting the delivery of the biologically active material therethrough.

10. The system of claim 9 wherein the electrode means further comprises control means capable of time-variable modulation of the applied charge.

11. The system of claim 10 wherein the biologically active materials include endothelial cells.

12. The system of claim 1 wherein the electrode means forms a layer parallel to the deployment layer and contains openings permitting the delivery of the biologically active material therethrough.

13. The system of claim 1 wherein the flow bypass means includes an elongated lumen connecting perfusion ports proximal and distal of the means for temporarily occluding blood flow.

14. The system of claim 2 wherein the flow bypass means includes an elongated lumen connecting perfusion ports proximal and distal of the means for temporarily occluding blood flow.

15. The system of claim 1 wherein the major arc is about 240°.

16. The system of claim 9 wherein the major arc is about 240°.

17. A method of providing iontophoretic transport to deliver biologically active material to a vascular segment of interest to restore vascular endothelium vitality in such specific segments of blood vessels comprising the steps of:

determining a vascular segment of interest to be treated;

navigating a vascular catheter device having spaced balloon elements expansible against the vessel walls to occlude blood flow therebetween, a chamber for delivering biologically active species to the vascular segment between the balloon elements, means for providing and delivering an electrical charge to the biologically active species during the deployment thereof and flow bypass means establishing an alternate path for flow about the occluded vascular segment to the predetermined vascular segment of interest;

expanding the balloon to occlude flow in the vascular segment of interest and establish bypass flow;

dispersing the biologically active species while using the electrode to deliver a charge to the material as desired;

deflating the balloons restoring normal vascular flow and removing the catheter device after a predetermined time necessary for the biologically active species to be sufficiently assimilated to be unaffected by normal vascular flow.

18. The method of claim 17 wherein the biologically active species includes endothelial cells and further comprising the step of modulating the charge supplied to the materials in a predetermined manner.

19. The method of claim 15 wherein the charge is delivered in a time-variable manner.

20. The method of claim 18 wherein the charge is delivered in a time-variable manner.

21. The method of claim 17 wherein the charge is pulsed or constant.

22. The method of claim 20 wherein the charge is pulsed or constant.

23. The method of claim 18 wherein the charge applied is negative or positive.

24. The method of claim 22 wherein the charge applied is negative or positive.

25. The method of claim 17 wherein the biologically active material includes material selected from the group consisting of metabolic activators and/or inhibitors and iontophoretic transportable pharmacologic agents.

26. The method of claim 24 wherein the charge is pulsed or constant.

* * * * *